United States Patent [19]
Vetter et al.

[11] Patent Number: 5,139,490
[45] Date of Patent: Aug. 18, 1992

[54] HYPODERMIC SYRINGE

[75] Inventors: Helmut Vetter, Ravensburg; Peter Geprägs, Weingarten, both of Fed. Rep. of Germany

[73] Assignee: Arzneimittel GmbH Apotheker Vetter & Co., Ravensburg, Fed. Rep. of Germany

[21] Appl. No.: 557,387

[22] Filed: Jul. 24, 1990

[30] Related U.S. Application Data
Jul. 27, 1989 [DE] Fed. Rep. of Germany .... 3924830

[51] Int. Cl.$^5$ .............................................. A61M 5/24
[52] U.S. Cl. .................................. 604/201; 604/232; 215/307; 220/204
[58] Field of Search .................... 604/232–235, 604/240, 241, 200, 201, 202, 204, 206, 218, 187, 407, 415; 215/307, 247; 220/366, 367, 204

[56] References Cited

U.S. PATENT DOCUMENTS

| | | | |
|---|---|---|---|
| 1,734,154 | 11/1929 | Brown | 604/206 |
| 2,102,704 | 12/1937 | Hein | 604/241 X |
| 2,483,825 | 10/1949 | Goldberg | 604/241 X |
| 2,526,365 | 10/1950 | Jorgenson | 604/232 X |
| 2,531,893 | 11/1950 | Roehr | 604/232 X |
| 3,757,779 | 9/1973 | Rovinski | 604/201 X |
| 3,811,441 | 5/1975 | Sarnoff | 604/201 |
| 4,193,402 | 3/1980 | Rumpler | 604/415 |
| 4,435,176 | 3/1984 | Ishikawa | 604/190 |
| 4,781,701 | 11/1988 | Geprägs | 604/240 X |
| 5,084,040 | 1/1992 | Sutter | 604/403 |

FOREIGN PATENT DOCUMENTS 0672607 12/1965 Belgium ............................. 604/233
0495067 11/1938 United Kingdom ................ 604/200

Primary Examiner—C. Fred Rosenbaum
Assistant Examiner—Mark O. Polutta
Attorney, Agent, or Firm—Herbert Dubno; Andrew M. Wilford

[57] ABSTRACT

A hypodermic-syringe assembly comprises a hard tubular body centered on an axis and having an axial front end formed with a radially inwardly projecting annular ridge and an axial rear end, a piston axially slidable in the body and normally adjacent the rear end, and a soft plug fitted in the front end in tight engagement with the ridge. The plug is formed with an axially rearwardly open blind passage having a front floor, and a front face defining with the passage floor a relatively thin membrane. Thus a needle can be poked through the membrane.

11 Claims, 3 Drawing Sheets

HYPODERMIC SYRINGE

FIELD OF THE INVENTION

The present invention related to a hypodermic syringe. More particularly this invention concerns such a syringe that is intended to be used once and then discarded.

BACKGROUND OF THE INVENTION

A standard hypodermic syringe comprises a cylindrically tubular body having a front end closed by or formed as a plug with a central throughgoing passage extending along the axis of the body and a rear end provided with a piston longitudinally axially displaceable in the body. A quantity of liquid to be injected is held in the body and a needle is fitted to the passage at its front end so that forward displacement of the piston by the plunger forces the liquid out of the body through the needle.

Such an item is typically provided as a prefilled disposable item in a hermetically sealed package. Thus it must be made at the lowest possible cost, whether it is set up for use with a simple needle cap or in a pen-type dosing injector of the type used by diabetics.

SUMMARY OF THE INVENTION

A hypodermic-syringe assembly according to the invention comprises a hard tubular body centered on an axis and having an axial front end formed with a radially inwardly projecting annular ridge and an axial rear end, a piston axially slidable in the body and normally adjacent the rear end, and a soft plug fitted in the front end in tight engagement with the ridge. The plug is formed with an axially rearwardly open blind passage having a front floor, and a front face defining with the passage floor a relatively thin membrane. Thus a needle can be poked through the membrane.

The assembly according to this invention can be made very cheaply simply by cutting pieces off a length of tubing to form the cylinder body. After it is cut off, the ends of the pieces are finished, the front plug is fitted in place, the medicament is filled into the tube, the piston is fitted, and the assembly is ready for sterilization and packaging. This can be done very cheaply. The assembly does not need to be opened; instead it is made ready by fitting a needle to it or dropping it into a pen-type multi-use device. The tight fit of the ridge on the body with the plug prevents it from moving axially as a needle or drain tube is poked through the membrane, and similarly when the syringe is being used the ridge prevents the plug from moving forward as the tube contents are pressurized and forced out of the needle.

According to another feature of this invention the passage is substantially cylindrical and centered on the axis and the floor is substantially planar and perpendicular to the axis. Furthermore the plug is formed with a radially outwardly open annular groove in which the body ridge fits. The body has at each end a beaded generally circular-section rim. Thus the plug can bear axially forward on the rim of the front end.

According to another feature of this invention the body is formed at its front end with a radially outwardly open groove and the assembly comprises a needle fitting engaged over the front end and formed with an inwardly protecting ridge engaged in the outwardly open groove. A finger support is carried on the body rear end.

For lyophilizing a medicament directly in the body of the syringe the plug is further formed with at least one radially extending passage opening radially outward on the plug and radially inward into the axial passage and with at least one radially outwardly open sawtooth groove axially rearward of the radial passage. The body in this case is formed with a rim bead engageable in the sawtooth groove in an advanced position of the plug. To prevent any undissolved particles from getting into the needle a filter is provided in the axial passage axially forward of the radial passage. Such a system is provided with a second piston to hold back a solvent that is only combined at use with the lyophilized drug in the front compartment.

DESCRIPTION OF THE DRAWINGS

The above and other objects, features, and advantages will become more readily apparent from the following, it being understood that any feature described with reference to one embodiment of the invention can be used where possible with any other embodiment and that reference numerals or letters not specifically mentioned with reference to one figure but identical to those of another refer to structure that is functionally if not structurally identical. In the accompanying drawing.

SPECIFIC DESCRIPTION

Figure 1:
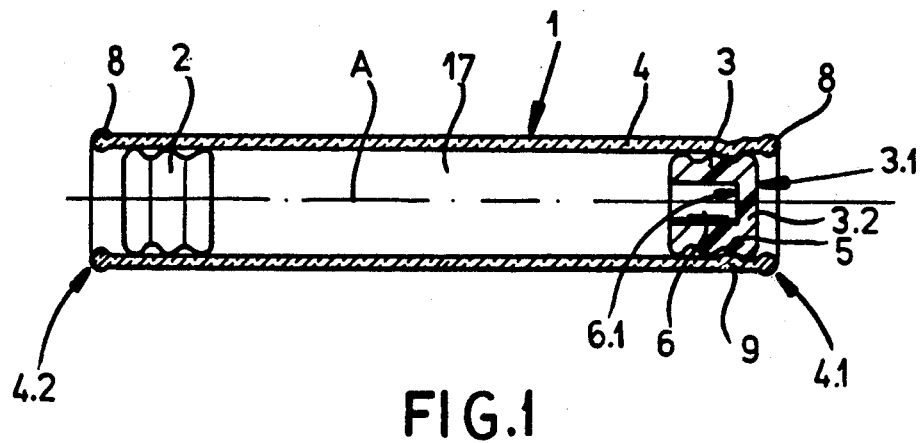
FIG. 1 is an axial section through a dose unit for a hypodermic assembly according to this invention.

As seen in FIG. 1 a dose unit for a hypodermic syringe according to this invention basically comprises a body 1 formed by a glass or plastic cylindrical tube 4 centered on an axis A and having a front end 4.1 closed by an elastomeric plug 3 and a rear end 4.2 closed by an elastomeric piston 2. The space 17 between the plug 3 and piston 4 is normally filled with a liquid medicament, for instance a single dose of insulin.

Both ends 4.1 and 4.2 are formed with circular-section beads 8 and the front end is formed with an inwardly projecting annular ridge 5 forming an outwardly open annular groove 9. The ridge 5 fits into a complementary annularly outwardly open groove on the plug 3. This plug 3 is formed centered on the axis A with a rearwardly open blind bore or passage 6 having a floor 6.1 extending perpendicular to the axis A. The plug 3 also has a front face 3.1 defining with the passage floor 6.1 a wall or membrane 3.2 that is fluid-tight.

Figure 2:
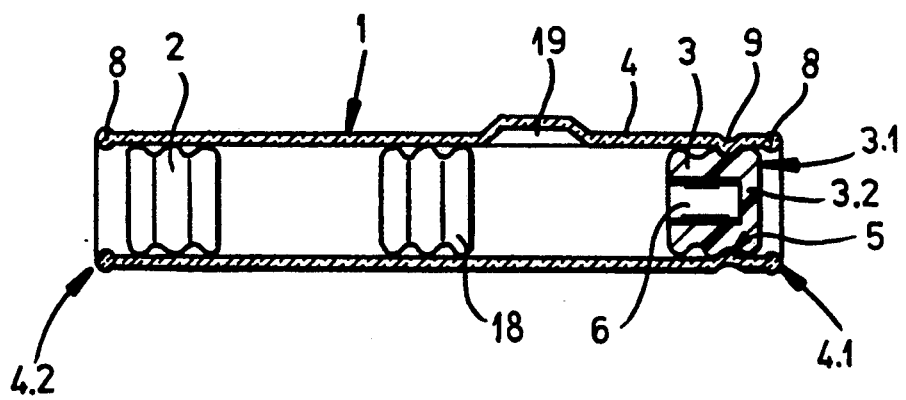
FIG. 2 is a view like FIG. 1 of a variant on the unit of FIG. 1.

It is also possible as shown in FIG. 2 and as described in copending U.S. patent application Ser. No. 07/524,347 filed May 16, 1990 to provide a second piston 18 in the body 1 and to form the body 4 forward of it with an inwardly open groove 19 for the mixing of substances to either axial side of this piston 18.

Figure 3:
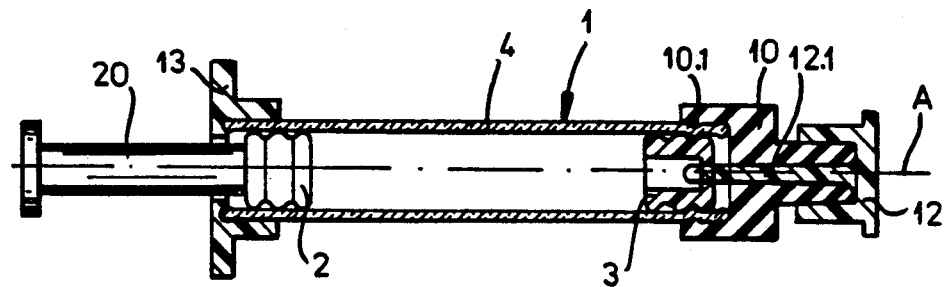
FIG. 3 is an axial section through a hypodermic assembly in accordance with the invention.

FIG. 3 shows how the front end 4.1 can be fitted with a cap 10 having an inwardly directed ridge 10.1 fitting in the groove 9 and itself carrying a tip cap 12 having a pin 12.1 projecting back through the plug 3. The rear end 4.2 is provided with a grip part 13 and a plunger 20 is fitted to the piston 2.

Figure 4:
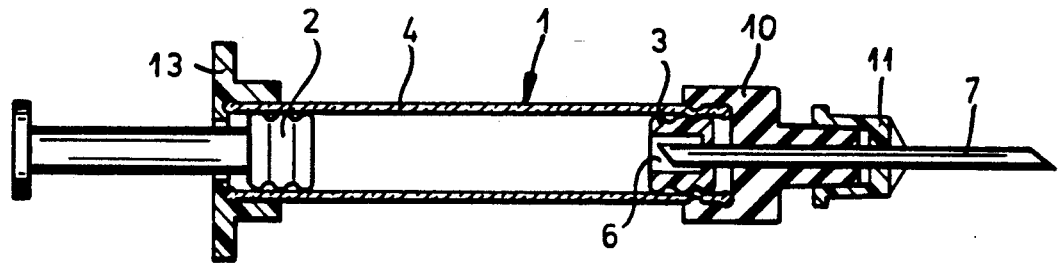
FIG. 4 is a view like FIG. 3 but with the needle in place.
Figure 5:
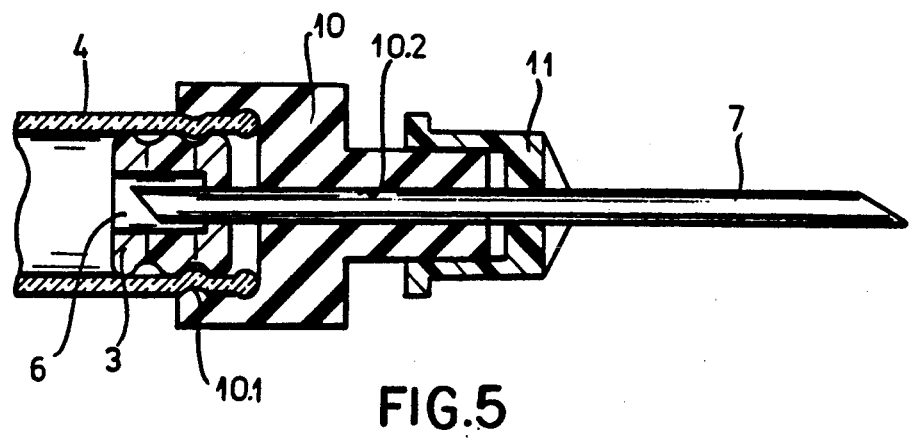
FIG. 5 is a large-scale view of a detail of FIG. 4.

In FIG. 4 instead of a tip cap 12 the assembly is provided with a cap 11 carrying a needle 7 that pokes back through the membrane 3.2. This cap 11 and needle 7 can be fitted to the assembly by the user. The needle 7 is fixed in a bore 0.2 (FIG. 5) formed on the axis A in the cap 10.

Figure 6:
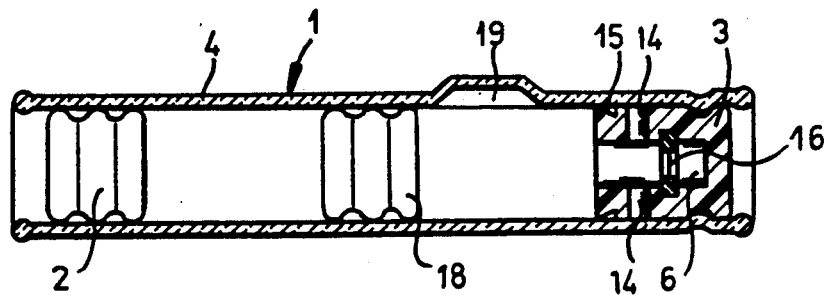
FIG. 6 is a view like FIGS. 1 and 2 of another system according to this invention.
Figure 7:
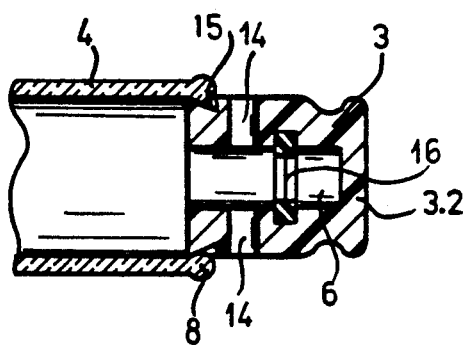
FIG. 7 is a large-scale view of the front end of the assembly of FIG. 6 in the drain position.
Figure 8:
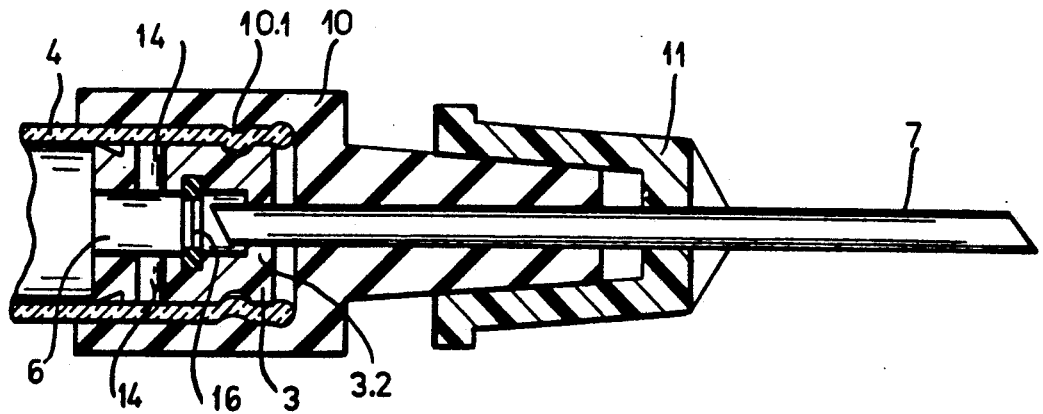
FIG. 8 is a large-scale view of the front end of the assembly of FIG. 6 with a needle mounted in position.

The arrangement of FIGS. 6 through 8 is intended for lyophilizing directly in the cylinder 1. To this end the plug 3 is formed with a pair of radial passages 14 opening externally on the outer surface of the plug and internally in the passage 6. In addition the outer surface is formed with a sawtooth groove 15 having a front perpendicular flank and a rear inclined flank. The front bead 8 fits in this groove 15 to hold the plug 3 in place while leaving the outer ends of the passages 14 exposed to the air. Thus it is possible to fill the compartment in front of the middle piston 18 with the medicament in solution and to lyophilize off the solution, allowing it to escape through the holes 14. Thereafter the plug 18 is pushed back to seal the container.

This arrangement is also provided with a small filter screen 16 in the passage 6 to avoid that any undissolved particles get into the needle 7 which, after passing through the membrane 3.2, stops short of this filter 16.

We claim:

1. A hypodermic-syringe cartridge assembly comprising:
   a hard tubular body centered on an axis and having an axial front end formed with a radially inwardly projecting annular ridge and an axial rear end, the body being formed at its front end with an inwardly projecting rim bead;
   a piston axially slidable in the body and normally adjacent the rear end; and
   a soft plug fitted in a use position of the assembly in the front end in tight engagement with the ridge, the plug being formed with
   a radially outwardly open annular front groove in which the ridge fits in the use position of the assembly,
   a radially open annular rear groove in which the rim bead fits in a treatment position of the assembly,
   an axially rearwardly open blind passage having a front floor,
   at least one radially extending passage opening radially outward on the plug between the plug grooves and radially inward into the axial passage, the tubular body covering the blocking the radial passage in the use position of the assembly, the radial passage being exposed forward of the tube front end in the treatment position of the assembly, whereby in the treatment position a liquid in the body can be lyophilized and escape through the radial passage which can thereafter be blocked by moving the plug back into the use position, and
   a front face defining with the passage floor a relatively thin membrane,
   whereby a needle can be poked through the membrane.

2. The syringe cartridge assembly defined in claim 1 wherein the passage is substantially cylindrical and centered on the axis and the floor is substantially planar and perpendicular to the axis.

3. The syringe cartridge assembly defined in claim 1 wherein the plug is formed with a radially outwardly open annular groove in which the body ridge fits.

4. The syringe cartridge assembly defined in claim 1 wherein in the use position the plug bears axially forward on the rim of the front end.

5. The syringe cartridge assembly defined in claim 1 wherein the body is formed at its front end with a radially outwardly open groove, the assembly further comprising:
   a needle fitting engaged over the front end and formed with an inwardly projecting ridge engaged in the outwardly open groove.

6. The syringe cartridge assembly defined in claim 1, further comprising
   a finger support carried on the body rear end.

7. The syringe assembly defined in claim 1 wherein the plug is further formed with
   at least one radially extending passage opening radially outward on the plug and radially inward into the axial passage.

8. The syringe assembly defined in claim 7 wherein the plug is further formed with
   at least one radially outwardly open sawtooth groove axially rearward of the radial passage,
   the body being formed with a rim bead engageable in the sawtooth groove in an advanced position of the plug.

9. The syringe cartridge assembly defined in claim 1, further comprising
   a filter in the axial passage axially forward of the radial passage.

10. A hypodermic-syringe assembly comprising:
    a hard tubular body centered on an axis and having an axial front end formed with a radially inwardly projecting annular ridge and an axial rear end, the body being formed at its front end with an inwardly projecting rim bead;
    a piston axially slidable in the body and normally adjacent the rear end;
    a soft plug fitted in the front end, the plug being formed with
    a radially outwardly open annular front groove in which the body ridge fits in a use position of the assembly,
    a radially open annular rear groove in which the rim bead fits in a treatment position of the assembly,
    an axially rearwardly open blind passage having a front floor,
    at least one radially extending passage opening radially outward on the plug between the plug grooves and radially inward into the axial passage, the tubular body covering blocking the radial passage in the use position of the assembly, the radial passage being exposed forward of the tube front end in the treatment position of the assembly, whereby in the treatment position in liquid in the body can be lyophilized and escape through the radial passage which can thereafter be blocked by moving the plug back into the use position, and
    a front face defining with the passage floor a relatively thin membrane,
    a needle fitting releasably engaged over the front end of the body; and a needle secured in the fitting and poking backward through the plug at the membrane.

11. A method of using a hypodermic cartridge assembly comprising:
- a hard tubular body centered on an axis and having an axial front end formed with a radially inwardly projecting annular ridge and an axial rear end, the body being formed at its front end with an inwardly projecting rim bead;
- a piston axially slidable in the body and normally adjacent the rear end; and
- a soft plug fitted in a use position of the assembly in the front end in tight engagement with the ridge, the plug being formed with
  - a radially outwardly open annular front groove in which the ridge fits in the use position of the assembly,
  - a radially open annular rear groove in which the rim bead fits in a treatment position of the assembly,
  - an axially rearwardly open blind passage having a front floor,
  - at least one radially extending passage opening radially outward on the plug between the plug grooves and radially inward into the axial passage, the tubular body covering the blocking the radial passage in the use position of the assembly, the radial passage being exposed forward of the tube front end in the treatment position of the assembly, and
  - a front face defining with the passage floor a relatively thin membrane, the method comprising the steps of sequentially:
- filling the tube with a liquid;
- setting the plug in the treatment position;
- treating the liquid such that vapors escape through the radial passage; and
- pushing the plug into the tubular body into the use position.

* * * * *

UNITED STATES PATENT AND TRADEMARK OFFICE
CERTIFICATE OF CORRECTION

PATENT NO. : 5,139,490
DATED : 18 August 1992
INVENTOR(S) : Helmut VETTER et al

It is certified that error appears in the above-indentified patent and that said Letters Patent is hereby corrected as shown below:

On the title page, item [73], the assignee should read as follows:

-- Arzneimittel GmbH Apotheker Vetter & Co. Ravensburg, Ravensburg, Fed. Rep. of Germany --.

Signed and Sealed this

Twenty-third Day of August, 1994

Attest:

BRUCE LEHMAN

Attesting Officer

Commissioner of Patents and Trademarks